United States Patent [19]

Nagel

[11] 4,429,116

[45] Jan. 31, 1984

[54] ALKYLATED OLEANDOMYCIN CONTAINING COMPOUNDS

[75] Inventor: Arthur A. Nagel, Gales Ferry, Conn.

[73] Assignee: Pfizer Inc., New York, N.Y.

[21] Appl. No.: 453,255

[22] Filed: Dec. 27, 1982

[51] Int. Cl.³ .............................................. C07H 17/08
[52] U.S. Cl. .................................... 536/7.2; 424/180
[58] Field of Search .......................... 536/7.2, 7.4, 7.1

[56] References Cited

U.S. PATENT DOCUMENTS

| | | | |
|---|---|---|---|
| 2,757,123 | 7/1956 | Sobin et al. | 167/65 |
| 3,022,219 | 2/1962 | Celmer | 167/65 |
| 3,884,903 | 5/1975 | Jones et al. | 536/7.2 |
| 4,125,705 | 11/1978 | Sciavolino | 536/7.4 |

*Primary Examiner*—Johnnie R. Brown
*Attorney, Agent, or Firm*—Charles J. Knuth; Albert E. Frost; James M. McManus

[57] ABSTRACT

A process for the alkylation of the $C_3''$ position of oleandomycin and antibacterial agents derived therefrom.

21 Claims, No Drawings

ALKYLATED OLEANDOMYCIN CONTAINING COMPOUNDS

FIELD OF THE INVENTION

This invention relates to novel $C_3''$ alkylated oleandomycin antibacterial agents and a process leading thereto and to certain 10- and 4''-epioleandomycin derivatives.

DESCRIPTION OF THE ART

Oleandomycin, its production in fermentation broths and its use as an antibacterial agent were first described in U.S. Pat. No. 2,757,123. The naturally occurring compound is known to have the following structure:

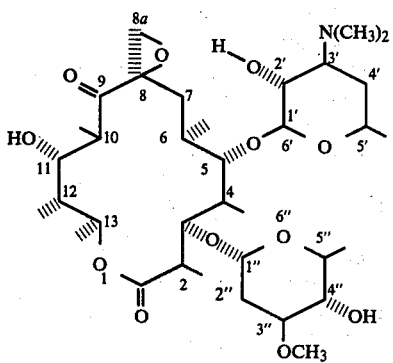

The conventionally accepted numbering scheme and stereochemical representation for oleandomycin and similar compounds is shown at a variety of positions.

Several synthetic modifications of this compound are known, particularly those in which from one to three of the free hydroxyl group found at the 2',4'' and 11-positions are esterified as acetyl esters. In addition, there are described in U.S. Pat. No. 3,022,219 similar modifications in which the acetyl in the above-mentioned esters is replaced with another, preferably unbranched lower alkanoyl of three to six carbon atoms.

More recently U.S. Pat. No. 4,125,705 reported the synthesis of 4''-deoxy-4''-amino-oleandomycin antibacterials through the corresponding 4''-deoxy-4''-oxo derivatives.

SUMMARY OF THE INVENTION

The present invention comprises a process for preparing compounds of the formula

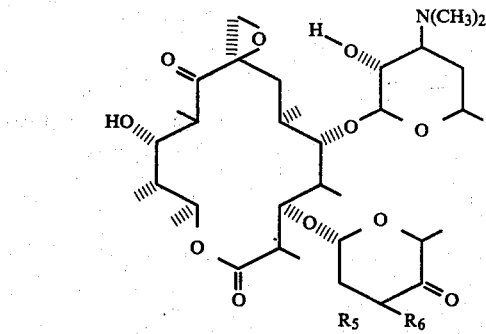

where $R_5$ is methyl, allyl or methoxy and $R_6$ is methoxy or allyl which comprises the steps of contacting one mole of a compound having the formula

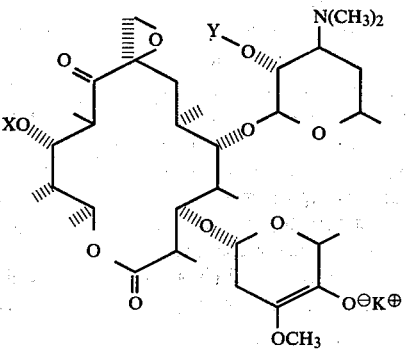

where Y is alkanoyl of two to three carbon atoms and X is trimethylsilyl with at least one mole of methyl iodide or allyl halide where said halide is chloro, bromo or iodo in a reaction inert solvent and temperature of about 0° C. to about 30° C.; removing the alkanoyl group by methanolysis; and removing the trimethylsilyl group with aqueous acid, with the proviso that when $R_6$ is allyl $R_5$ is methoxy.

Preferred features of this process include the use of tetrahydrofuran as the reaction inert solvent and reaction temperature of about 20° C. The preferred alkylating agents are methyl iodide and allyl bromide.

The semisynthetic macrolide antibacterial agents and intermediates of the present invention are represented by the formulae

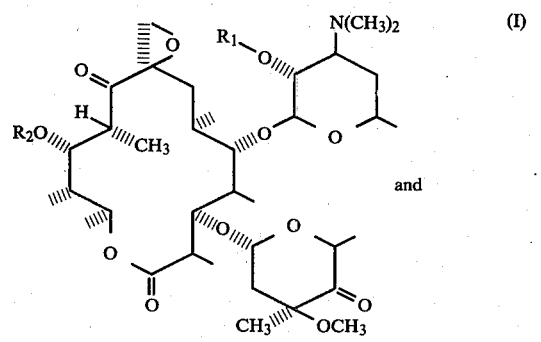

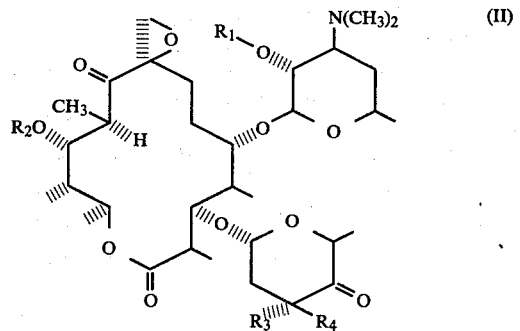

and the pharmaceutically acceptable acid addition salts thereof, where $R_1$ is hydrogen or alkanoyl of two to three carbon atoms; $R_2$ is hydrogen or trimethylsilyl; $R_3$ is hydrogen, methyl, allyl or methoxy; and $R_4$ is methoxy or allyl with the proviso that when R$_4$ is allyl, R$_3$ is methoxy and when R$_2$ is hydrogen R$_1$ is hydrogen.

Preferred compounds of formula I are those where R$_1$ is acetyl and R$_2$ is trimethylsilyl and where R$_1$ and R$_2$ are each hydrogen.

A preferred group of compounds of formula II are those where R$_1$ is acetyl and R$_2$ is trimethylsilyl. Especially preferred within this group are those compounds where R$_3$ is hydrogen and R$_4$ is methoxy; where R$_3$ is methyl and R$_4$ is methoxy; where R$_3$ is allyl and R$_4$ is methoxy; and where R$_3$ is methoxy and R$_4$ is allyl.

A second group of preferred compounds are those of formula II where R$_1$ and R$_2$ are each hydrogen. Especially preferred within this group are those compounds where R$_3$ is methyl and R$_4$ is methoxy; where R$_3$ is allyl and R$_4$ is methoxy; and where R$_3$ is methoxy and R$_4$ is allyl.

A second group of semisynthetic macrolide antibacterial agents and intermediates of the present invention are represented by the formula

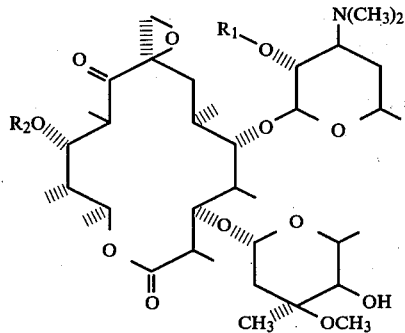

and the pharmaceutically acceptable acid addition salt thereof, where R$_1$ is hydrogen or alkanoyl having two to three carbon atoms and R$_2$ is hydrogen or trimethylsilyl with the proviso that when R$_2$ is hydrogen R$_1$ is hydrogen.

Especially preferred are those compounds where both R$_1$ and R$_2$ are hydrogen and where R$_1$ is acetyl and R$_2$ is trimethylsilyl.

DETAILED DESCRIPTION OF THE INVENTION

In the first preliminary step of the instant process the appropriate 11-trimethylsilyl-2'-alkanoyl-4"-deoxy-4"-oxo-oleandomycin intermediate is converted to the required potassium salt on treatment with potassium hydride. In practice, a cooled solution of the aforementioned intermediate in tetrahydrofuran, a preferred solvent for this process, is treated with the requisite alkylating agent followed by potassium hydride. Alternately, the potassium hydride can be added first followed by the alkylating agent. The reaction mixture is allowed to warm and is then quenched with water. The intermediate 11-trimethylsilyl-2'-alkanoyl-3"-alkylated macrolide is isolated and purified by conventional means.

In the initial step of the instant process about equimolar amounts of the macrolide, alkylating agent and potassium hydride are employed. Small increases in the molar amount of any one of these reagents does not markedly effect the reaction course.

The reaction can be conducted over a wide temperature range. Temperature of 0° to 30° C. are operable, with a preferred range of about 20° C. Employing these reaction temperatures, the alkylation is complete in 30 to 60 minutes.

The solvent should be a reaction inert solvent. By such a solvent is meant one which solubilizes the appropriate reagents to some extent, but does not react to any appreciable extent with either the starting reagents or final product. Solvents or mixtures thereof which are suitable include aromatic solvents such as toluene, and ethers such as tetrahydrofuran and diethyl ether. The preferred solvent is tetrahydrofuran.

The second step in the instant process comprises removal of the 2'-alkanoyl group from the 11-trimethylsilyl-2'-alkanoyl-3"-alkylated macrolide intermediate. This is achieved by methanolysis and comprises allowing the intermediate to stir in a methanol solution for 18-46 hours at ambient temperatures.

The trimethylsilyl group is removed from the alkylated intermediate by treating the methanol solution with water and sufficient acid to give a pH of about 2.5. After exposure to the acid for 30-60 minutes the pH is adjusted to about 8.5 with base and the product isolated and purified by known methods.

The instantly claimed process allows for the synthesis of novel macrolides having a second substituent at the 3"-position. It was unexpected that such an alkylation would occur at that position since it appeared equally probable that alkylation could take place at the 5"-position, the 10-position or at the 3'-dimethylamino group. A further advantage of the instant process is that the alkylation occurs predominantly at the 3"-position to the exclusion of any other position in the macrolide structure.

As for the structural assignments, all the data suggests that methylation of the 3"-position introduces the methyl substituent in the axial position. When the alkylation process is carried out with an allyl halide both the axial and equatorial epimers are formed and can be readily separated.

Further, it has been noted that when the process of the present invention is conducted with an excess amount, i.e., 75–100% excess, of potassium hydride, the methyl substituent at the 10-position is epimerized to the S configuration (J.A.C.S, 88, 1797 1965), giving rise to a novel 10-epi, 3"-methylated oleandomycin type antibacterial agent.

It has further been found that the 3"-methylated oleandomycin products of the instant process can, on treatment with hydrogen in the presence of a Raney nickel catalyst, be converted to the corresponding 3"-methylated-4"-epi-oleandomycin.

This latter process is carried out by shaking an ethanolic solution of a 11-trimethylsilyl-2'-alkanoyl-3"-dehydro-3"-methyl-4"-deoxy-4"-oxo oleandomycin with a two fold, by weight, of a Raney nickel sludge in a hydrogen atmosphere at an initial pressure of 50 psi at ambient temperatures for about 16 to 20 hours.

Following completion of the reaction the spent catalyst is filtered and the solvent evaporated to give the desired product. If desired, the resulting product can be further purified by chromatography.

Removal of the trimethylsilyl and alkanoyl groups are carried out by the previously described methods, thereby giving rise to novel macrolide antibacterial agents.

The reagents for the processes leading to the intermediate and products of the present invention are known in the art or are prepared by conventional means. The preparation of 2'-acetyl-4"-deoxy-4"-oxo oleandomycin is reported in U.S. Pat. No. 4,125,705.

Preferred among the intermediates of the present invention are 11-trimethylsilyl-2'-acetyl-4"-deoxy-4"-oxo-oleandomycin, 11-trimethylsilyl-2'-acetyl-3"-dehydro-3"-methyl-4"-deoxy-4"-oxo-oleandomycin, 11-trimethylsilyl-2'-acetyl-3"-dehydro-3"-allyl-4"-deoxy-4"-oxo-oleandomycin, 11-trimethylsilyl-2'-acetyl-3"-dehydro-3"-allyl-3"-epi-4"deoxy-4"-oxo-oleandomycin, 10-epi-11-trimethylsilyl-2'-acetyl-4"-deoxy-4"-oxo-oleandomycin and 11-trimethylsilyl-2'-acetyl-3"-dehydro-3"-methyl-4"-epi-oleandomycin.

Preferred among the antibacterial compounds of the present invention are 3"-dehydro-3"-methyl-4"-deoxy-4"-oxo-oleandomycin, 3"-dehydro-3"-allyl-4"-deoxy-4"-oxo-oleandomycin, 3"-dehydro-3"-allyl-3"-epi-4"-deoxy-4"-oxo-oleandomycin, 10-epi-3"-dehydro-3"-methyl-4"-deoxy-4"-oxo-oleandomycin and 3"-dehydro-3"-methyl-4"-epi-oleandomycin.

In the utilization of the chemotherapeutic activity of those compound of the present invention which form salts, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically acceptable bases by decomposition of the salt as described above, or alternately they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic, gluconic and aspartic acids.

The novel oleandomycin derivatives described herein exhibit in vitro activity against a variety of Gram-positive microorganisms such as *Staphylococcus aureus* and *Streptococcus pyogenes* and against certain Gram-negative microorganisms such as those of spherical ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sickroom utensils; and an industrial antimicrobials, for example, in water treatment, slime control, paint and wood preservation.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Gram-positive and certain Gram-negative microorganisms in vivo such as *Staphalococcus aureus* via the oral and/or parenteral routes of administration in animals, including man. Their in vivo activity is more limited as regards susceptible organisms and is determined by the usual procedure which comprises treating mice of substantially uniform weight with the test organism and subsequently treating them orally or subcutaneously with the test compound. In practice, the mice, e.g., 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour postinoculation, and is repeated 4 and 24 hours later. Surviving mice are held for four days after the last treatment and the number of survivors is noted.

When used in vivo, these novel compounds can be administered orally or parenterally, e.g., by subcutaneous or intramuscular injection, at a dosage of from about 100 mg/kg to about 200 mg/kg of body weight per day. The favored dosage range is from about 150 mg/kg to about 200 mg/kg of body weight per day. Vehicles suitable for parenteral injection may be either aqueous such as water, isotonic saline, isotonic dextrose, Ringers' solution, or non-aqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspension. In general, the compounds are used in various dosage forms at concentration levels ranging from about 0.5 percent to about 90 percent by weight of the total composition.

The following examples are provided solely for the purpose of further illustration. Nuclear magnetic resonance spectra (NMR) were measured at 60 to 100 MHz for solutions in deuterochloroform ($CDCl_3$), perdeutero dimethyl sulfoxide (DMSO-$D_6$) or deuterium oxide ($D_2O$) or are noted otherwise, and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quartet; m, multiplet.

EXAMPLE 1

11-Trimethylsilyl-2'-acetyl-4"-deoxy-4"-oxo-oleandomycin

To 36 ml. of dimethylformamide and 30 ml. of tetrahydrofuran containing 60 g. (0.083 mole) of 2'-acetyl-4"-deoxy-4"-oxo-oleandomycin (U.S. Pat. No. 4,125,705) and 12.0 g. (0.12 mole) of imidazole and cooled to $-10°$ C. was added 14 ml. (0.11 mole) of trimethylsilyl chloride in 10 ml. of tetrahydrofuran at such a rate that the reaction temperature could be kept at less than 5° C. When the addition was complete, the reaction was allowed to stir at about 15° C. for 1 hour.

The reaction mixture was poured into a mixture of 300 ml. of ethyl acetate and 300 ml. of water. The aqueous layer was extracted further with fresh ethyl acetate (2×200 ml.) and the organic extracts combined, washed with a brine solution (3×200 ml.) and dried over sodium sulfate. Removal of the solvent in vacuo gave 61.2 g. of the desired intermediate.

The NMR spectrum (CDCl$_3$) showed absorption at 0.13 (s, 9H), 2.06 (s, 3H), 2.28 (s, 6H) and 3.5 (s, 3H) ppm.

EXAMPLE 2

11-Trimethylsilyl-2'-acetyl-3"-dehydro-3"-methyl-4"-deoxy-4"-oxo-oleandomycin

To a solution of 8.0 g. (10 mmoles) of 11-trimethylsilyl-2'-acetyl-4"-deoxy-4"-oxo-oleandomycin in 35 ml. of dry tetrahydrofuran was added 2.5 ml. (40 mmoles) of methyl iodide and the solution cooled to −70° C. Potassium hydride (520 mg., 13 mmoles) suspended in 10 ml. of dry tetrahydrofuran was added portion-wise to the reaction mixture such that the temperature did not rise above −60° C. When the addition was complete the mixture was allowed to warm slowly to −20° C.

The reaction was quenched under nitrogen by the addition of 10 ml. of water, and the reaction mixture added to a mixture of 200 ml. of water and 200 ml. of ethyl acetate. The organic phase was separated, dried and concentrated in vacuo to a yellow foam. The residue was triturated with petroleum ether and filtered. The filtrate was concentrated to dryness to give 5.0 g. of crude product.

The residual product was chromatographed on 100 g. of chloroform packed silica gel using ethyl acetate as the eluent. Fractions (9 ml. each) 41–56 were collected and concentrated to give 820 mg. of pure intermediate.

The NMR spectrum (CDCl$_3$) showed absorption at 0.12 (s, 9H), 2.01 (s, 3H), 2.25 (s, 6H) and 3.16 (s, 3H) ppm.

Fractions 35–40 and 57–80 were collected, combined and concentrated to give 1.1 g. of less pure intermediate.

EXAMPLE 3

3"-Dehydro-3"-methyl-4"-deoxy-4"-oxo-oleandomycin

A solution of 20 ml. of methanol containing 820 mg. (1 mmole) of 11-trimethylsilyl-2'-acetyl-3"-dehydro-3"-methyl-4"-deoxy-4"-oxo-oleandomycin was allowed to stir at room temperature for 18 hours. The methanol was removed in vacuo and the residue treated with 20 ml. of tetrahydrofuran and 10 ml. of water. The pH of the resulting solution was adjusted to 2.5 with 1 N hydrochloric acid and the reaction mixture allowed to stir for 60 minutes at room temperature. The pH was adjusted to 8.0 with 1 N aqueous sodium hydroxide and the solution treated with 50 ml. of water. The product was extracted with ethyl acetate and the extracts combined, dried and concentrated to give 600 mg. of a foam. Recrystallization from diethyl ether gave 380 mg. of the pure product, m.p. 282°–283° C.

Anal. Calcd. for $C_{36}H_{61}O_{12}N$: C, 61.8; H, 8.7; N, 2.0. Found: C, 61.2; H, 8.8; N, 2.2.

The NMR spectrum (CDCl$_3$) showed absorption at 2.26 (s, 6H), 3.16 (s, 3H) and 5.53 (q, 1H) ppm.

EXAMPLE 4

11-Trimethylsilyl-2'-acetyl-3"-dehydro-3"-methyl-4"-epi-oleandomycin

A mixture of 1.5 g. (1.8 mmoles) of 11-trimethylsilyl-2'-acetyl-3"-dehydro-3"-methyl-4"-deoxy-4"-oxo-oleandomycin in 20 ml. of ethanol and 3.0 g. of a Raney nickel sludge was shaken in a hydrogen atmosphere at an initial pressure of 50 psi. After 18 hours the reaction mixture was filtered and the filtrate concentrated to give 1.4 g. of crude product.

A 200 mg. sample was chromatographed on 8 g. of silica gel using ethyl acetate-acetone (9:1, v:v) as the eluent. Fractions (5 ml. each) 18–22 were combined and concentrated to give 100 mg. of the desired intermediate.

The remainder of the crude product, when chromatographed in a similar manner gave 470 mg. of the desired intermediate.

The NMR spectrum (CDCl$_3$) showed absorption at 0.12 (s, 9H), 2.11 (s, 3H), 2.33 (s, 6H) and 3.30 (s, 3H) ppm.

EXAMPLE 5

3"-Dehydro-3"-methyl-4"-epi-oleandomycin

In a manner similar to Example 3, 470 mg. (0.58 mmole) of 11-trimethylsilyl-2'-acetyl-3"-dehydro-3"-methyl-4"-epi-oleandomycin in 30 ml. of methanol was allowed to stir at room temperature for 18 hours. The methanol was removed under vacuum and the residue dissolved in 20 ml. of tetrahydrofuran. To the resulting solution was added 20 ml. of water and sufficient 1 N hydrochloric acid to give pH 2.5. The reaction mixture was allowed to stir for 60 minutes at room temperature and the pH adjusted to 8.5 with aqueous sodium hydroxide. Water (50 ml.) was added and the product extracted with ethyl acetate. The extracts were combined and concentrated to give 380 gm. of the desired product.

The NNR spectrum (CDCl$_3$) showed absorption at 2.28 (s, 6H), 3.21 (s, 3H) and 5.53 (q, 1H) ppm.

EXAMPLE 6

A.

11-Trimethylsilyl-2'-acetyl-3"-dehydro-3"-allyl-4"-deoxy-4"-oxo oleandomycin

To 2.7 g. (3.4 mmoles) of 11-trimethylsilyl-2'-acetyl-4"-deoxy-4"-oxo-oleandomycin in 15 ml. of dry tetrahydrofuran cooled to 5° C. was added a suspension of 225 mg. (5.6 mmoles) of potassium hydride in 5 ml. of the same solvent. After one minute 0.48 ml. (5.6 mmoles) of allyl bromide was added and the reaction mixture allowed to warm to 20° C. The reaction was then quenched with 15 ml. of water and the reaction mixture poured into a mixture of 100 ml. of water and 100 ml. of ethyl acetate. The organic phase was concentrated to give 2.2 g. of a foam.

The reaction was rerun starting with 6 g. (7.5 mmoles) of ketone and a proportioned amount of other reagents to give 5.7 g. of crude product.

The products (2.2 g. and 5.7 g.) were combined and chromatographed on 450 g. of silica gel using ethyl acetate as the eluent. Fractions (10 ml. each) 206–240 were combined and concentrated to yield 700 mg. of the desired intermediate.

The NMR spectrum (CDCl$_3$) showed absorption at 0.13 (s, 9H), 2.06 (s, 3H), 2.3 (s, 6H) and 3.13 (s, 3H) ppm.

B.
11-Trimethylsilyl-2'-acetyl-3''-dehydro-3''-allyl-3''-epi-4''-deoxy-4''-oxo-oleandomycin Fractions 331–360 were combined and concentrated to give 260 mg. of the desired intermediate.

The NMR spectrum (CDCl$_3$) showed absorption at 0.12 (s, 9H), 2.10 (s, 3H), 2.31 (s, 6H) and 3.75 (s, 3H).

EXAMPLE 7

3''-Dehydro-3''-allyl-4''-deoxy-4''-oxo-oleandomycin

A solution of 700 mg. of 11-trimethylsilyl-2'-acetyl-3''-dehydro-3''-allyl-4''-deoxy-4''-oxo-oleandomycin in 50 ml. of methanol was allowed to stir at room temperature for 42 hours. Water (50 ml.) was added and the pH adjusted to 2.5 using 1 N hydrochloric acid. After stirring at room temperature for 45 minutes the reaction mixture was extracted with ethyl acetate. The pH of the aqueous layer was adjusted to 8.5 with 1 N aqueous sodium hydroxide and again extracted with ethyl acetate. The ethyl acetate extracts were combined, dried over sodium sulfate and concentrated to give 500 mg. of the desired product.

The NMR spectrum (CDCl$_3$) showed absorption at 2.30 (s, 6H), 3.13 (s, 3H) and 5.66 (q, 1H) ppm.

EXAMPLE 8

3''-Dehydro-3''-allyl-3''-epi-4''-deoxy-4''-oxo-oleandomycin

In a manner similar to Example 7, 260 mg. of 11-trimethylsilyl-2'-acetyl-3''-dehydro-3''-allyl-3''-epi-4''-deoxy-4''-oxo-oleandomycin gave 130 mg. of the desired product.

The NMR spectrum (CDCl$_3$) showed absorption at 2.30 (s, 6H), 3.21 (s, 3H) and 5.66 (q, 1H) ppm.

EXAMPLE 9

10-Epi-11-trimethylsilyl-2'-acetyl-3''-dehydro-3''-methyl-4''-deoxy-4''-oxo-oleandomycin A solution of 20 ml. of dry benzene containing 3.2 g. (4 mmoles) of 11-trimethylsilyl-2'-acetyl-4''-deoxy-4''-oxo-oleandomycin was cooled to 10° C. and treated with 290 mg. (7.25 mmoles) of potassium hydride suspended in 5 ml. of dry benzene. After 1.5 minutes a solution of 0.75 ml. (12 mmoles) of methyl iodide in 5 ml. of dry benzene was added. The cooling bath was removed and the reaction mixture allowed to stir for 30 minutes and warm to room temperature. The reaction was quenched with 10 ml. of water and the reaction mixture extracted with ethyl acetate. The extracts were combined, dried over sodium sulfate and concentrated in vacuo giving 2.8 g. of crude intermediate.

The residue was triturated with petroleum ether and filtered. The filtrate was concentrated to dryness and the residue chromatographed on 100 g. of silica gel using ethyl acetate as the eluent. Fractions (6 ml. each) 129–145 were combined and concentrated to give 500 mg. of the desired intermediate.

The NMR spectrum (CDCl$_3$) showed absorption at 0.12 (s, 9H), 2.01 (s, 3H), 2.25 (s, 6H) and 3.08 (s, 3H) ppm.

EXAMPLE 10

10-Epi-3''-dehydro-3''-methyl-4''-deoxy-4''-oxo-oleandomycin

A solution of 500 mg. of 10-epi-11-trimethylsilyl-2'-acetyl-3''-dehydro-3''-methyl-4''-deoxy-4''-oxo-oleandomycin in 25 ml. of methanol was allowed to stir at room temperature for 34 hours. The methanol was removed under vacuum and the residual foam treated with 20 ml. of tetrahydrofuran and 5 ml. of water. Sufficient 1 N hydrochloric acid was added to give a pH of 2.5 and the mixture allowed to stir for 45 minutes. The pH was then adjusted to 9.5 with 1 N aqueous sodium hydroxide and the mixture treated with 75 ml. of water and 75 ml. of ethyl acetate. The organic phase was dried and concentrated to dryness.

The residual was redissolved in 10 ml. of ethyl acetate, combined with 30 ml. of water and the pH adjusted to 2.5. The aqueous phase was separated and combined with 30 ml. of ethyl acetate and the pH adjusted to 8.5. The organic phase was separated, dried and concentrated to give 380 mg. of the desired product.

Anal. Calcd. for $C_{36}H_{61}O_{12}N$: C, 61.8; H, 8.7; N, 2.0. Found: C, 60.4; H, 8.6; N, 2.0.

The NMR spectrum (CDCl$_3$) showed absorption at 2.25 (s, 6H), 3.05 (s, 3H) and 5.58 (q, 1H) ppm.

I claim:

1. A compound selected from the group consisting of an oleandomycin derivative of the formulae:

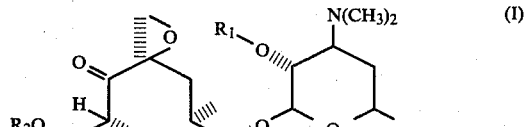

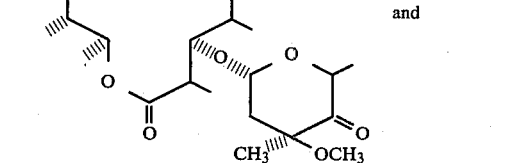

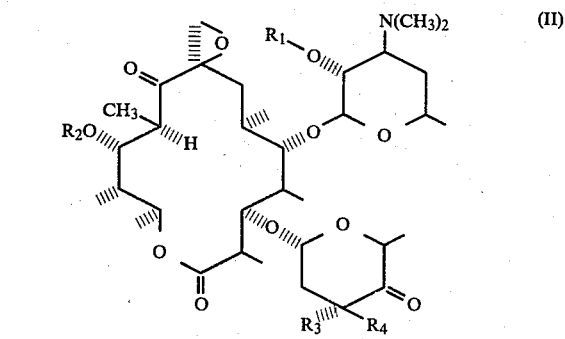

and a pharmaceutically acceptable acid addition salt thereof wherein
  $R_1$ is selected from the group consisting of hydrogen and alkanoyl having two to three carbon atoms;
  $R_2$ is trimethylsilyl;
  $R_3$ is selected from the group consisting of hydrogen, methyl, allyl and methoxy; and
  $R_4$ is selected from the group consisting of methoxy and allyl;
  with the proviso that when $R_4$ is allyl, $R_3$ is methoxy.

2. A compound of claim 1, formula II.

3. A compound of claim 2, wherein $R_1$ is acetyl and $R_2$ is trimethylsilyl.

4. The compound of claim 3, wherein $R_3$ is hydrogen and $R_4$ is methoxy.

5. The compound of claim 3, wherein $R_3$ is methyl and $R_4$ is methoxy.

6. The compound of claim 3, wherein $R_3$ is allyl and $R_4$ is methoxy.

7. The compound of claim 3, wherein $R_3$ is methoxy and $R_4$ is allyl.

8. A compound of claim 2, wherein $R_1$ is hydrogen.

9. The compound of claim 8, wherein $R_3$ is methyl and $R_4$ is methoxy.

10. The compound of claim 8, wherein $R_3$ is allyl and $R_4$ is methoxy.

11. The compound of claim 8, wherein $R_3$ is methoxy and $R_4$ is allyl.

12. A compound of claim 1, formula I.

13. The compound of claim 12, wherein $R_1$ is acetyl and $R^2$ is trimethylsilyl.

14. The compound of claim 12, wherein $R_1$ is hydrogen.

15. A compound selected from the group of oleandomycin derivatives of the formula:

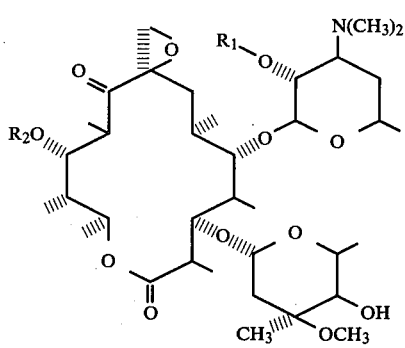

and the pharmaceutically acceptable acid addition salt thereof, wherein $R_1$ is selected from the group consisting of hydrogen and alkanoyl having two to three carbon atoms; and $R_2$ is selected from the group consisting of hydrogen and trimethylsilyl.

with the proviso that when $R_2$ is hydrogen $R_1$ is hydrogen.

16. The compound of claim 15, wherein $R_1$ and $R_2$ are each hydrogen.

17. The compound of claim 15, wherein $R_1$ is acetyl and $R_2$ is trimethylsilyl.

18. A process for preparing a compound selected from an oleandomycin derivative of the formula

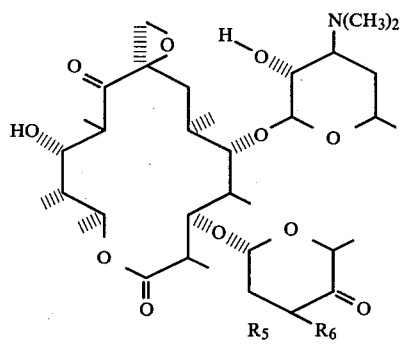

wherein $R_5$ is selected from the group consisting of methyl, allyl and methoxy; and $R_6$ is selected from the group consisting of methoxy and allyl which comprises the steps of contacting one mole of a compound of the formula

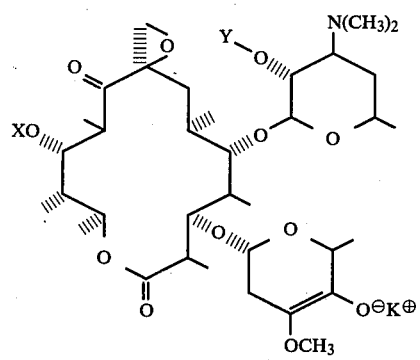

wherein Y is alkanoyl having two to three carbon atoms and X is trimethylsilyl with at least one mole of an alkylating agent selected from the group consisting of methyl iodide and an allyl halide wherein said halide consists of chloro, bromo or iodo in a reaction inert solvent and temperature of about 0° C. to about 30° C.; removing the alkanoyl group by methanolysis; and removing the trimethylsilyl group with aqueous acid, with the proviso that when $R_6$ is allyl $R_5$ is methoxy.

19. The process of claim 18, wherein the reaction inert solvent is tetrahydrofuran and reaction temperature 20° C.

20. The process of claim 19, wherein the alkylating agent is methyl iodide.

21. The process of claim 19, wherein the alkylating agent is allyl bromide.

* * * * *